United States Patent
Friedman et al.

(10) Patent No.: US 8,038,593 B2
(45) Date of Patent: Oct. 18, 2011

(54) SYSTEM AND METHOD FOR NETWORK MONITORING OF MULTIPLE MEDICAL DEVICES

(75) Inventors: Gregory S. Friedman, La Jolla, CA (US); Kraldon Ferch, Carlsbad, CA (US)

(73) Assignee: CareFusion 303, Inc., San Diego, CA (US)

( * ) Notice: Subject to any disclaimer, the term of this patent is extended or adjusted under 35 U.S.C. 154(b) by 143 days.

(21) Appl. No.: 11/006,116

(22) Filed: Dec. 6, 2004

(65) Prior Publication Data

US 2005/0137653 A1    Jun. 23, 2005

Related U.S. Application Data

(60) Provisional application No. 60/527,152, filed on Dec. 5, 2003.

(51) Int. Cl.
*A61M 21/00* (2006.01)
*A61M 31/00* (2006.01)

(52) U.S. Cl. ............... 600/26; 604/65; 600/300

(58) Field of Classification Search .......... 607/30, 607/31, 59; 600/301
See application file for complete search history.

(56) References Cited

U.S. PATENT DOCUMENTS

| | | | |
|---|---|---|---|
| 2,141,006 A | 12/1938 | Marinsky | |
| 3,724,455 A | 4/1973 | Unger | |
| 3,831,006 A | 8/1974 | Chaffin, III et al. | |
| 3,848,112 A | 11/1974 | Weichselbaum et al. | |
| 3,872,448 A | 3/1975 | Mitchell, Jr. | |
| 3,898,984 A | 8/1975 | Mandel et al. | |
| 3,910,260 A | 10/1975 | Sarnoff et al. | |
| 3,921,196 A | 11/1975 | Patterson | |
| 3,970,996 A | 7/1976 | Yasaka et al. | |
| 4,051,522 A | 9/1977 | Healy et al. | |
| 4,135,241 A | 1/1979 | Stanis et al. | |

(Continued)

FOREIGN PATENT DOCUMENTS

EP            0 192 786 B1       9/1986

(Continued)

OTHER PUBLICATIONS

PCT/US2004/040950 PCT International Search Report Date Jul. 19, 2005 and Written Opinion of the International Searching Authority (PCT Rule 43*bis*.1) (9 pages).

(Continued)

*Primary Examiner* — Carl H. Layno
*Assistant Examiner* — Jon-Eric C. Morales
(74) *Attorney, Agent, or Firm* — McDermott Will & Emery LLP (57) ABSTRACT

The present invention provides for a system an method of monitoring the status of a plurality of medical devices connected to a central computer or server using a wired or wireless network, and displaying information representative of the status of the medical devices to a user on a display screen using both graphics and text. The system is also capable of determining when a condition or alarm warranting notification of the care giver to correct the condition exists, and displaying information about the condition or alarm on the display, including associating a warning graphic or icon representative of the condition or alarm with an icon representing a specific medical device or portion of a medical device. The system includes a rules data base and decision engine that may be used to determine the existence of conditions that require notification to the care giver.

11 Claims, 9 Drawing Sheets

U.S. PATENT DOCUMENTS

| | | | |
|---|---|---|---|
| 4,164,320 A | 8/1979 | Irazoqui et al. | |
| 4,216,462 A | 8/1980 | McGrath et al. | |
| 4,237,344 A * | 12/1980 | Moore ............................ | 379/38 |
| 4,315,309 A | 2/1982 | Coli | |
| 4,321,461 A | 3/1982 | Walter, Jr. et al. | |
| 4,360,125 A | 11/1982 | Martindale et al. | |
| 4,373,527 A | 2/1983 | Fischell | |
| 4,476,381 A | 10/1984 | Rubin | |
| 4,604,847 A | 8/1986 | Moulding, Jr. et al. | |
| 4,636,950 A | 1/1987 | Caswell et al. | |
| 4,674,652 A | 6/1987 | Aten et al. | |
| 4,688,026 A | 8/1987 | Scribner et al. | |
| 4,695,954 A | 9/1987 | Rose et al. | |
| 4,696,671 A | 9/1987 | Epstein et al. | |
| 4,731,726 A | 3/1988 | Allen, III | |
| 4,733,364 A | 3/1988 | Yamagata | |
| 4,778,449 A | 10/1988 | Weber et al. | |
| 4,785,969 A | 11/1988 | McLaughlin | |
| 4,803,625 A | 2/1989 | Fu et al. | |
| 4,810,243 A | 3/1989 | Howson | |
| 4,828,545 A | 5/1989 | Epstein et al. | |
| 4,831,562 A | 5/1989 | McIntosh et al. | |
| 4,835,372 A | 5/1989 | Gombrich et al. | |
| 4,839,806 A | 6/1989 | Goldfischer et al. | |
| 4,847,764 A | 7/1989 | Halvorson | |
| 4,850,009 A | 7/1989 | Zook et al. | |
| 4,853,521 A | 8/1989 | Claeys et al. | |
| 4,855,909 A | 8/1989 | Vincent et al. | |
| 4,857,713 A | 8/1989 | Brown | |
| 4,857,716 A | 8/1989 | Gombrich et al. | |
| 4,865,584 A | 9/1989 | Epstein et al. | |
| 4,882,575 A | 11/1989 | Kawahara | |
| 4,899,839 A | 2/1990 | Dessertine et al. | |
| 4,916,441 A | 4/1990 | Gombrich et al. | |
| 4,918,604 A | 4/1990 | Baum | |
| 4,925,444 A | 5/1990 | Orkin et al. | |
| 4,942,544 A | 7/1990 | McIntosh et al. | |
| 4,967,928 A | 11/1990 | Carter | |
| 4,970,669 A | 11/1990 | McIntosh et al. | |
| 4,978,335 A | 12/1990 | Arthur, III | |
| 5,001,630 A | 3/1991 | Wiltfong | |
| 5,006,699 A | 4/1991 | Felkener et al. | |
| 5,036,462 A | 7/1991 | Kaufman et al. | |
| 5,036,852 A | 8/1991 | Leishman | |
| 5,072,383 A | 12/1991 | Brimm et al. | |
| 5,078,683 A | 1/1992 | Sancoff et al. | |
| 5,088,056 A | 2/1992 | McIntosh et al. | |
| 5,088,981 A | 2/1992 | Howson et al. | |
| 5,100,380 A | 3/1992 | Epstein et al. | |
| 5,126,957 A | 6/1992 | Kaufman et al. | |
| 5,142,484 A | 8/1992 | Kaufman et al. | |
| 5,153,416 A | 10/1992 | Neeley | |
| 5,153,827 A | 10/1992 | Coutre et al. | |
| 5,164,575 A | 11/1992 | Neeley et al. | |
| 5,166,498 A | 11/1992 | Neeley | |
| 5,171,977 A | 12/1992 | Morrison | |
| 5,207,642 A * | 5/1993 | Orkin et al. ..................... | 604/65 |
| 5,235,507 A | 8/1993 | Sackler et al. | |
| 5,256,157 A | 10/1993 | Samiotes et al. | |
| 5,258,906 A | 11/1993 | Kroll et al. | |
| 5,265,010 A | 11/1993 | Evans-Paganelli et al. | |
| 5,267,174 A | 11/1993 | Kaufman et al. | |
| 5,291,399 A | 3/1994 | Chaco | |
| 5,292,029 A | 3/1994 | Pearson | |
| 5,307,263 A | 4/1994 | Brown | |
| 5,314,243 A | 5/1994 | McDonald et al. | |
| 5,315,505 A | 5/1994 | Pratt et al. | |
| 5,317,506 A | 5/1994 | Coutre et al. | |
| 5,319,363 A | 6/1994 | Welch et al. | |
| 5,331,547 A | 7/1994 | Laszlo | |
| 5,356,378 A | 10/1994 | Doan | |
| 5,367,555 A | 11/1994 | Isoyama | |
| 5,368,554 A | 11/1994 | Nazarian et al. | |
| 5,371,692 A | 12/1994 | Draeger et al. | |
| 5,374,813 A | 12/1994 | Shipp | |
| 5,378,231 A | 1/1995 | Johnson et al. | |
| 5,390,238 A | 2/1995 | Kirk | |
| 5,401,059 A | 3/1995 | Ferrario | |
| 5,404,384 A | 4/1995 | Colburn et al. | |
| 5,408,443 A | 4/1995 | Weinberger | |
| 5,412,372 A | 5/1995 | Parkhurst et al. | |
| 5,412,564 A | 5/1995 | Ecer | |
| 5,416,695 A | 5/1995 | Stutman et al. | |
| 5,456,691 A | 10/1995 | Snell | |
| 5,465,082 A | 11/1995 | Chaco | |
| 5,472,614 A | 12/1995 | Rossi | |
| 5,473,536 A * | 12/1995 | Wimmer ........................ | 700/90 |
| 5,502,944 A | 4/1996 | Kraft et al. | |
| 5,515,426 A | 5/1996 | Yacenda et al. | |
| 5,533,079 A | 7/1996 | Colburn et al. | |
| 5,536,084 A | 7/1996 | Curtis et al. | |
| 5,538,006 A | 7/1996 | Heim et al. | |
| 5,542,420 A | 8/1996 | Goldman et al. | |
| 5,544,661 A | 8/1996 | Davis et al. | |
| 5,547,470 A | 8/1996 | Johnson et al. | |
| 5,561,412 A | 10/1996 | Novak et al. | |
| 5,562,232 A | 10/1996 | Pearson | |
| 5,564,803 A | 10/1996 | McDonald et al. | |
| 5,592,374 A | 1/1997 | Fellegara et al. | |
| 5,594,786 A | 1/1997 | Chaco | |
| 5,597,995 A | 1/1997 | Williams et al. | |
| 5,622,429 A | 4/1997 | Heinze | |
| 5,630,710 A | 5/1997 | Tune et al. | |
| 5,633,910 A | 5/1997 | Cohen | |
| 5,643,212 A | 7/1997 | Coutre et al. | |
| 5,644,778 A | 7/1997 | Burks et al. | |
| 5,655,118 A | 8/1997 | Hendel et al. | |
| 5,657,236 A | 8/1997 | Conkright | |
| 5,658,250 A | 8/1997 | Blomquist et al. | |
| 5,672,154 A | 9/1997 | Sillen et al. | |
| 5,681,285 A | 10/1997 | Ford et al. | |
| 5,689,229 A | 11/1997 | Chaco et al. | |
| 5,692,640 A | 12/1997 | Caulfield et al. | |
| 5,699,038 A | 12/1997 | Ulrich et al. | |
| 5,703,786 A | 12/1997 | Conkright | |
| 5,710,551 A | 1/1998 | Ridgeway | |
| 5,721,913 A | 2/1998 | Ackroff et al. | |
| 5,737,539 A | 4/1998 | Edelson | |
| 5,738,102 A | 4/1998 | Lemelson | |
| 5,752,235 A | 5/1998 | Kehr et al. | |
| 5,758,095 A | 5/1998 | Albaum et al. | |
| 5,758,096 A | 5/1998 | Barsky et al. | |
| 5,760,704 A | 6/1998 | Barton et al. | |
| 5,772,585 A | 6/1998 | Lavin et al. | |
| 5,774,865 A | 6/1998 | Glynn | |
| 5,781,442 A | 7/1998 | Engleson | |
| 5,790,409 A | 8/1998 | Fedor et al. | |
| 5,803,906 A | 9/1998 | Pratt et al. | |
| 5,819,229 A | 10/1998 | Boppe | |
| 5,822,418 A | 10/1998 | Yacenda et al. | |
| 5,822,544 A | 10/1998 | Chaco | |
| 5,833,599 A | 11/1998 | Schrier et al. | |
| 5,842,173 A | 11/1998 | Strum et al. | |
| 5,842,976 A | 12/1998 | Williamson | |
| 5,845,253 A | 12/1998 | Rensimer et al. | |
| 5,845,255 A | 12/1998 | Mayaud | |
| 5,845,264 A | 12/1998 | Nellhaus | |
| 5,850,344 A | 12/1998 | Conkright | |
| 5,852,408 A | 12/1998 | Christiansen et al. | |
| 5,855,550 A | 1/1999 | Lai et al. | |
| 5,867,821 A | 2/1999 | Ballantyne et al. | |
| 5,883,806 A | 3/1999 | Meador et al. | |
| 5,895,371 A | 4/1999 | Levitas | |
| 5,899,998 A | 5/1999 | McGauley et al. | |
| 5,903,211 A | 5/1999 | Flego et al. | |
| 5,905,653 A | 5/1999 | Higham et al. | |
| 5,907,490 A | 5/1999 | Oliver | |
| 5,911,132 A | 6/1999 | Sloane | |
| 5,911,687 A | 6/1999 | Sato et al. | |
| 5,912,818 A | 6/1999 | McGrady | |
| 5,920,054 A | 7/1999 | Uber, III | |
| 5,930,145 A | 7/1999 | Yuyama et al. | |
| 5,935,099 A | 8/1999 | Peterson et al. | |
| 5,942,986 A | 8/1999 | Shabot et al. | |
| 5,950,630 A | 9/1999 | Portwood et al. | |
| 5,950,632 A | 9/1999 | Reber et al. | |
| 5,954,641 A | 9/1999 | Kehr et al. | |

| | | | | | | |
|---|---|---|---|---|---|---|
| 5,961,446 | A | 10/1999 | Beller et al. | EP | 0 652 528 A2 | 5/1995 |
| 5,971,593 | A | 10/1999 | McGrady | EP | 0 784 283 B1 | 7/1997 |
| 5,995,077 | A | 11/1999 | Wilcox et al. | EP | 1 003 121 A2 | 10/1998 |
| 6,000,828 | A | 12/1999 | Leet | EP | 0 921 488 A1 | 6/1999 |
| 6,003,006 | A | 12/1999 | Colella | EP | 1 018 347 B1 | 7/2000 |
| 6,009,333 | A | 12/1999 | Chaco | GB | 2 141 006 A | 12/1984 |
| 6,021,392 | A | 2/2000 | Lester | JP | 03-099536 | 4/2003 |
| 6,024,699 | A | 2/2000 | Surwit et al. | WO | WO 92/04806 | 3/1992 |
| 6,032,155 | A | 2/2000 | de la Huerga | WO | WO 93/22735 | 11/1993 |
| 6,039,251 | A | 3/2000 | Holowko et al. | WO | WO 94/05344 | 3/1994 |
| 6,048,087 | A | 4/2000 | Laurent et al. | WO | WO 94/08647 | 4/1994 |
| 6,053,887 | A | 4/2000 | Levitas | WO | WO 94/13250 | 6/1994 |
| 6,063,026 | A | 5/2000 | Schauss et al. | WO | WO 95/23378 | 8/1995 |
| 6,082,776 | A | 7/2000 | Feinberg | WO | WO 96/20745 | 7/1996 |
| 6,112,182 | A | 8/2000 | Akers et al. | WO | WO 96/25214 | 8/1996 |
| 6,135,949 | A | 10/2000 | Russo et al. | WO | WO 96/36923 | 11/1996 |
| 6,269,340 | B1 | 7/2001 | Ford et al. | WO | WO 97/04712 | 2/1997 |
| 6,282,441 | B1 | 8/2001 | Raymond et al. | WO | WO 98/13783 | 4/1998 |
| 6,292,698 | B1 | 9/2001 | Duffin et al. | WO | WO 98/28676 | 7/1998 |
| 6,302,844 | B1 | 10/2001 | Walker et al. | WO | WO 99/09505 | 2/1999 |
| 6,312,378 | B1 | 11/2001 | Bardy | WO | WO 99/10829 | 3/1999 |
| 6,319,200 | B1 | 11/2001 | Lai et al. | WO | WO 99/10830 | 4/1999 |
| 6,322,502 | B1 | 11/2001 | Schoenberg et al. | WO | WO 99/35588 | 7/1999 |
| 6,757,898 | B1 * | 6/2004 | Ilsen et al. ............... 709/203 | WO | WO 99/44167 | 9/1999 |
| 6,785,589 | B2 | 8/2004 | Eggenberger et al. | WO | WO 99/45490 | 9/1999 |
| 6,847,861 | B2 | 1/2005 | Lunak et al. | WO | WO 99/46718 | 9/1999 |
| 7,060,031 | B2 * | 6/2006 | Webb et al. ............... 600/300 | WO | WO 99/67732 | 12/1999 |
| 2002/0120676 | A1 * | 8/2002 | Biondi et al. ............... 709/203 | WO | WO 00/03344 | 1/2000 |
| 2002/0123673 | A1 * | 9/2002 | Webb et al. ............... 600/300 | WO | WO 00/04521 | 1/2000 |
| 2002/0169636 | A1 | 11/2002 | Eggers et al. | WO | WO 00/18449 | 4/2000 |
| 2003/0036683 | A1 * | 2/2003 | Kehr et al. ............... 600/300 | WO | WO 00/32088 | 6/2000 |
| 2003/0105555 | A1 | 6/2003 | Lunak et al. | WO | WO 00/32098 | 6/2000 |
| 2003/0135087 | A1 * | 7/2003 | Hickle et al. ............... 600/26 | | | |

FOREIGN PATENT DOCUMENTS

| | | |
|---|---|---|
| EP | 0 384 155 B1 | 2/1989 |
| EP | 0 595 474 A2 | 5/1994 |
| EP | 0 649 316 B1 | 4/1995 |

OTHER PUBLICATIONS

European Patent Office Examination Report dated May 29, 2007 (2 pages).

* cited by examiner

SYSTEM AND METHOD FOR NETWORK MONITORING OF MULTIPLE MEDICAL DEVICES

CROSS-REFERENCES TO RELATED APPLICATIONS

This application claims priority to provisional application No. 60/527,152, filed Dec. 5, 2003, the contents of which are hereby incorporated herein by reference.

FIELD OF THE INVENTION

The invention is related generally to monitoring multiple medical devices, and more particularly, to a system and method for providing information about the status of multiple medical devices which can be accessed at locations of choice by the user.

BACKGROUND OF THE INVENTION

The delivery of therapy and the collection of patient data from bedside equipment, laboratory equipment and institutional information systems has become more integrated with the advent of more capable and reliable computer networks, faster and larger storage media, and the miniaturization of computer processors and memory. This technology has resulted in the inclusion of computer processors or microprocessors and memory in a wide variety of medical equipment. Inclusion of communications capability allows the processors and memory in the medical equipment to be tied into ward, department and institution wide networks. These networks allow for the exchange of information between various institutional information systems and individual medical devices. The devices may be therapy delivery devices, such as infusion pumps, or they may be vital signs measurement and data collection devices, including both bedside monitors and laboratory equipment.

As the complexity of therapeutic medication delivery has increased, one problem that has arisen is that there are more opportunities for error. Many different systems have been proposed to address the frequency of the medication error, such as the system described in U.S. Patent Publication No. 2002/0169636 entitled "System and Method for Managing Patient Care" by Eggers, the subject matter of which is intended to be, and is, incorporated into and is a part of the subject matter of this provisional patent application.

One problem that occurs with systems having many client medical devices is that it is necessary to ensure that the memory of the various devices on the system are updated frequently enough so that the devices have access to up-to-date patient information, therapeutic information, rule sets and patient specific medication guidelines. Until recently, it has been necessary for servers to poll each device connected to a network to determine if the device was connected to the network, and to then send the device any updated information. Such polling is resource and time intensive, and may decrease the efficiency and speed of the entire network.

This problem is particularly difficult where the medical devices utilize a media other than a hard wired network, such as a wireless network, or the internet. In these systems, individual medical devices may call the server through an access point of the wireless network, or over the internet, using either a dial-up, cable, DSL or wireless connection. In such systems, there is a potential security problem in that the networks are essentially wide open to requests for communication that come from an external source. The system must determine whether the communication request is coming from a secure medical device, or some un-secure source which should be prevented from establishing communication with the server.

Another problem that occurs in a busy medical institution is that as new systems are brought on line, they must compete for scarce space within the institution. Until recently, however, while technology has existed to allow medical devices to be operated in a remote and/or mobile fashion, capable of being moved throughout an institution, and then connecting to an institution's network using wired or wireless access points, the servers connected to the network commonly had to be permanently located in one area of the institution. Even where the servers could be moved, such movement typically required shutting down the system, disconnecting the server from the network, and then reconnecting the server at the new location. Such relocation typically requires relocation and reconfiguration of other network resources, such as hard wiring or optical cabling and routers.

In an increasing number of clinical settings, it is becoming desirable to network multiple medical devices, such as infusion pumps and vital signs monitors, so that they may be remotely monitored by clinic personnel. For example, pharmacists, nurses, physicians, biomedical technicians, and others may have a need to be able to monitor the status of medical infusion pumps or monitors in the clinics. Each may have a different reason for monitoring the medical devices, yet all may need to see their status. To reduce patient disturbance and to increase efficiency for the various clinic personnel, it would be desirable for all infusion pumps to be operatively connected through some type of network, either hard wired or wireless. The present invention fulfills these and other needs.

SUMMARY OF THE INVENTION

The present invention includes a system and method for monitoring the status of a plurality of medical devices and providing a visual display of information gathered during that monitoring to a care giver to assist the care giver in assessing the status of the therapy given to patients in an institution. The medical devices monitored may include devices configured to deliver therapeutic treatment to the patients, as well as clinical assessment devices, such as vital signs monitors, laboratory instruments, and the like. The visual display is designed to provide an overview of all medical devices that are in communication with a server, and provide both iconic and textual representations of the status of the medical devices. Additionally, the visual display includes the ability display warning symbols, graphics or text associated with various conditions that have been identified as requiring notice to be given to care givers so that appropriate actions may be taken to correct the condition.

In one aspect, the present invention includes a system for monitoring multiple medical devices comprising a server to which the multiple medical devices are in communication; a program running on the server configured to obtain status from each medical device and make the status available to users of the program, the program providing a listing of all medical devices identified to the server, the program being responsive to a selection of a medical device that is identified, and the program providing status and other information about the selected medical device in graphic and text forms.

In another aspect, the present invention includes a medical monitoring system, comprising at least one medical device; a server in communication with the medical device; a display screen in communication with server; and a program running on a processor in communication with the server to program the processor to monitor information communicated by the at least one medical device representative of a status of the at least one medical device, the program also programming the processor to generate a graphical display for communicating the information to a user. In still another aspect, the graphical display includes a plurality of portions, with at least one portion including an icon representative of the medical device. In another aspect, the graphical display includes at least one portion providing a textual description of the status of the medical device, and in yet another aspect, the graphical display includes at least one portion providing a status of all channels of the medical device.

In yet another aspect, the processor is programmed to generate a warning symbol and associate the symbol with the icon representative of the medical device. In still another aspect, the processor compares a value of a parameter associated with the status of the at least one medical device with a database of rules to determine if the value of the parameter is within a range of values defined by a rule in the database of rules, and if the value of the parameter is not within the range of values, generates the warning symbol. In an additional aspect, the icon is representative of a fluid level in a fluid source.

In a further aspect, the present invention includes a medical device monitoring system, comprising a medical device, the medical device including a wireless communication means for communicating information to and from the medical device; a central computer including a wireless communication means for communicating information to and from the central computer, the central computer also including a program running on the central computer for communicating with the medical device, including querying the medical device about the status of the medical device and for receiving information from the medical device representative of the status of the medical device, and for generating a visual display of the received information to a user. In one aspect of the present invention, the central computer is a mobile server capable of moving about a facility wherein the medical device is located. In another aspect, the visual display includes a plurality of portions providing information representative of the medical device to the user. In another aspect, the visual display includes a plurality of portions, with at least one portion including an icon representative of the medical device. In still another aspect, at least one other portion of the plurality of portions provides a textual description of the status of the medical device, and in another aspect, at least one portion of the display includes the icon and a textual description of the status of the medical device.

In a further aspect, the central computer includes means for accessing rules stored in a data base of rules, the rules including ranges of values for operating parameters of the medical device. Additionally, the program running on the central computer may also compare values of the information received from the medical device to the rules stored in the data base of rules and generates a warning graphic if a value of a selected operating parameter of the received information is not within the range of values contained in a selected rule. In some aspects of the present invention, the warning graphic may be associated with the icon representative of the medical device.

In still another aspect, the present invention includes a method of displaying information related to the status of medical devices operating in an institution comprising establishing communications between the medical devices and a server; receiving information representative of a status of the medical devices; displaying an icon representing each medical device communicating with the server in one portion of a visual display; selecting an icon representing a selected medical device; displaying an enlarged graphic depicting the selected medical device in another portion of the visual display; and displaying selected information representative of the status of the medical device in another portion of the visual display. In one variation, displaying selected information representative of the status of the medical device includes displaying at least one icon and also displaying text descriptive of the selected information.

In a still further aspect, the method of the present invention further includes determining if the information received from the medical device includes information indicative of a condition requiring an alarm to be provided and displaying an icon representative of the alarm in at least one portion of the visual display.

These and other advantages of the invention will become apparent from the following more detailed description when taken in conjunction wit the accompanying drawings of illustrative embodiments.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

As will be appreciated by one of skill in the art, the present invention may be embodied as a method, data processing system, or computer program product. Accordingly, the present invention may take the form of an entirely hardware embodiment, an entirely software embodiment, or an embodiment combining software and hardware aspects. Furthermore, the present invention may take the form of a computer program product on a computer-usable storage medium having computer readable program code means embodied in the medium. Any suitable computer readable medium may be utilized including, but not limited to, hard disks, CD-ROMs, optical storage devices, and magnetic storage devices and the like.

The present invention is described below with reference to flowchart illustrations of methods, apparatus (systems), and computer program products according to an embodiment of the invention. It will be understood that each block of the flowchart illustrations, and combinations of blocks in the flowchart illustrations, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

The present invention can be implemented as a system running on a stand alone computing device. Preferably, the present invention is implemented as a system in a client-server environment. As is known to those of skill in the art, a client application is the requesting program in a client-server relationship. A server application is a program that awaits and fulfills requests from client programs in the same or other computers. Client-server environments may include public networks, such as the Internet, and private networks often referred to as "intranets", local area networks (LANs) and wide area networks (WANs), virtual private networks (VPNs), frame relay or direct telephone connections. It is understood that a client application or server application, including computers hosting client and server applications, or other apparatus configured to execute program code embodied within computer usable media, operates as means for performing the various functions and carries out the methods of the various operations of the present invention.

The following terms and definitions are useful in fully understanding the various aspects and embodiments of the present invention. Accordingly, these terms are intended, for the purposes of describing the present invention, to have the meanings set forth as follows:

AES means Advanced Encryption Standard. AES is a next-generation replacement for the Defense Encryption Standard (DES), and is a highly-secure symmetric block encryption algorithm approved by the Federal Information Processing Standard and the National Institute of Standards and Technology.

CBC means Cipher Block Chaining. CBC is a mode of operation for block ciphers where each block of plaintext is XORed with the previously encoded block of ciphertext, before it is encoded.

DHCP means Dynamic Host Configuration Protocol. DHCP provides for dynamically assigning IP addresses to clients on an IP network.

ECB means Electronic Cook Book. ECB is a mode of operation for blocking ciphers where each block of plaintext is encoded independently of all other blocks.

IP means Internet Protocol. IP is a simple addressing protocol used to deliver network messages. Many versions of IP exists, and the various embodiments of the present invention are intended to operate using any version of IP, and preferably version 4 (IPv4).

LAN means Local Access Network. A LAN is a group of systems connected over a private, homogenous network.

MD5 stands for the MD5 Message Digest Algorithm. MD5 is a complex hashing algorithm designed to produce a secure and unique "fingerprint" of a given data set.

NIM means network interface module, and is a device that allows medical devices to connect to and participate on an IP network.

RDS stands for Remote Data Server, typically a central server that serves as a proxy for all third party communication with networked medical devices.

TCP means Transmission Control Protocol. TCP is a high level protocol that provides a persistent, reliable stream-based data connection between two clients on a network.

UDP stands for User Datagram Protocol. UDP is a low-level protocol that provides relatively unreliable message-based communications between clients on a network.

Figure 1:
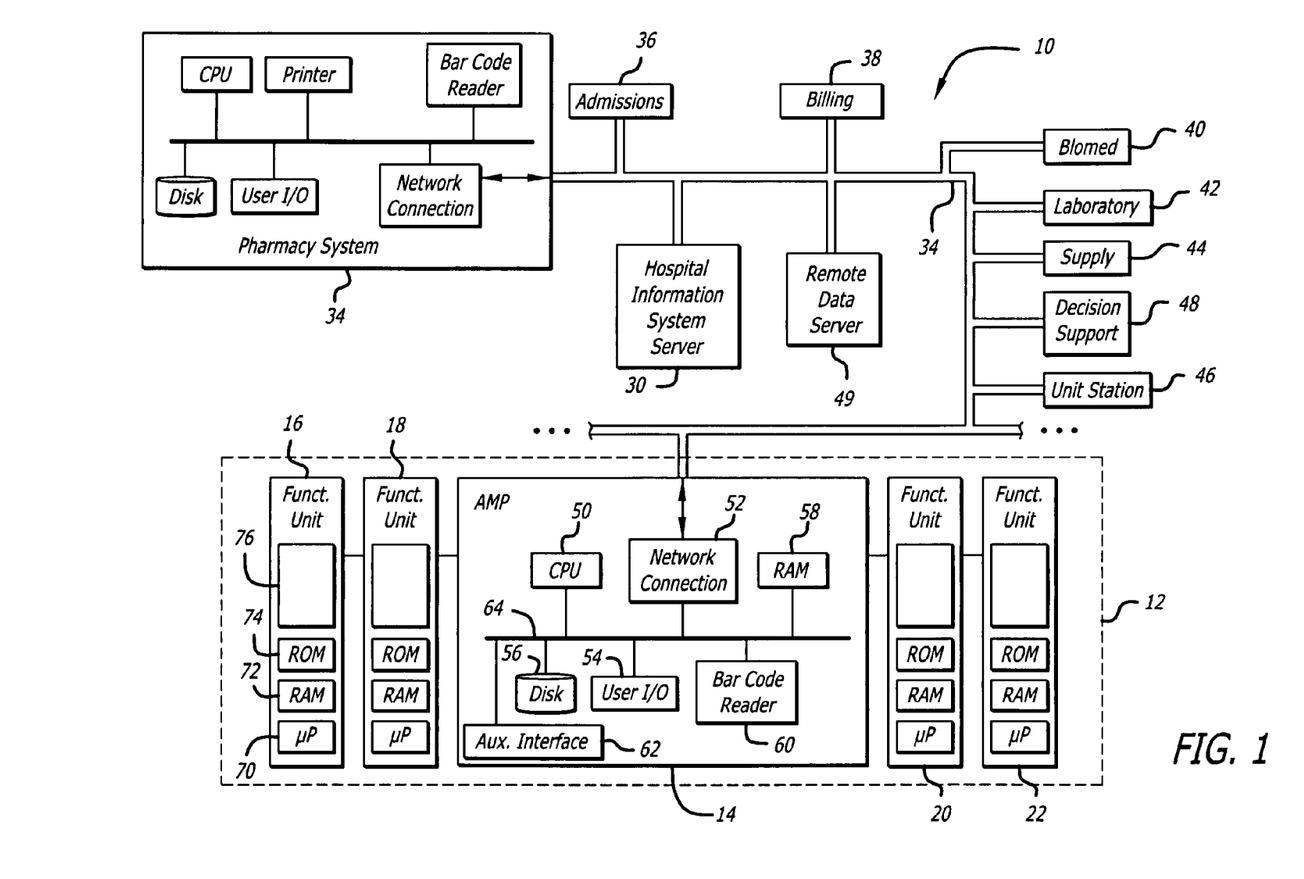
FIG. 1 is a graphical illustration of a patient care system utilizing various aspects of the present invention.

FIG. 1 is a general illustration of a patient care system utilizing aspects of the present invention. In FIG. 1, a patient care device 12 is connected to a hospital network 10 including a pharmacy management system 34 and a hospital information system server 30. Each element 12, 30 and 34 is connected to network 10 by a transmission channel 32. Transmission channel 32 is any wired or wireless transmission channel, for example a 802.11 wireless local area network (LAN). In an embodiment of the present invention, network 10 also includes computer systems located in various departments throughout a hospital. For example, network 10 of FIG. 1 optionally includes computer systems associated with an admissions department 36, a billing department 38, a biomedical engineering department 40, a clinical laboratory 42, a central supply department 44, one or more unit station computers and/or a medical decision support system 48. Additionally, the system may incorporate a separate remote data server 49, the function of which will be described in more detail below. Moreover, although the remote data server 49 is shown as a separate server, the functions and programming of the remote data server 49 may be incorporated into another computer, such as, for example, the hospital information system server 30, if such is desired by engineers designing the institution's information system.

Patient care device 12 preferably comprises a system similar to that described in U.S. Pat. No. 5,713,856 to Eggers et al., which is incorporated herein by reference. Alternatively, other patient care devices, such as pumps, physiological monitors (e.g., heart rate, blood pressure, ECG, EEG, pulse oximeter, and other patient monitors), therapy devices, and other drug delivery devices may be utilized according to the teachings set forth herein. Patient care device 12 preferably comprises a control module 14, also referred to as interface unit 14, connected to one or more functional modules 16, 18, 20, 22. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also preferably, although not necessarily, includes a main non-volatile storage unit 56, preferably a hard disk drive, for storing software and data and one or more internal buses 64 for interconnecting the aforementioned elements.

In a typical embodiment, user interface device 54 is a touch screen for displaying information to a user and allowing a user to input information by touching defined areas of the screen. Alternatively, user interface device 54 could include any means for displaying and inputting information, such as a monitor, a printer, a keyboard, softkeys, a mouse, a track ball and/or a light pen. Coded data input device 60 is preferably a bar code reader capable of scanning and interpreting data printed in bar coded format. Alternatively, data input device 60 could be any device for entering coded data into a computer, such as devices for reading a magnetic strips, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and coded data input device 60 may be the same device. Alternatively, although data input device 60 is shown in FIG. 1 to be disposed within interface unit 14, one skilled in the art will recognize that data input device 60 may be integral within pharmacy system 34 or located externally and communicating with pharmacy system 34 through an RS-232 serial interface or any other appropriate communication means. Auxiliary interface 62 is preferably an RS-232 communications interface, however any other means for communicating with a peripheral device such as a printer, patient monitor, infusion pump or other medical device may be used without departing from the scope of the invention. Additionally, data input device 60 may be a separate functional module, such as modules 16, 18, 20 and 22, and configured to communicate with controller 14, or any other system on the network, using suitable programming and communication protocols.

Network connection 52 is preferably a direct network connection such as a T1 connection, an integrated services digital network (ISDN) connection, a digital subscriber line (DSL) modem or a cable modem. Alternatively, any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Alternatively, functional module 18, 20 and/or 22 may be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 are connected physically and electronically in serial fashion to one or both ends of interface unit 14 as shown in FIG. 1 and as detailed in Eggers et al. However, one skilled in the art will recognize that there are other means for connecting functional modules with the interface unit that may be utilized without departing from the scope of the invention. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 typically includes module-specific components 76, a microprocessor 70, a volatile memory 72 and a nonvolatile memory 74 for storing information. It should be noted that while four functional modules are shown in FIG. 1, any number of devices may be connected directly or indirectly to central controller 14. The number and type of functional modules described herein are intended to be illustrative, and in no way limit the scope of the present invention. Module-specific components 76 include any components necessary for operation of a particular module, such as a pumping mechanism for infusion pump module 16.

While each functional module is typically capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Patient care device 12 is capable of operating in several different modes, or personalities, with each personality defined by a configuration database. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from pharmacy 34, admissions 36, laboratory 42, and the like.

Figure 2:
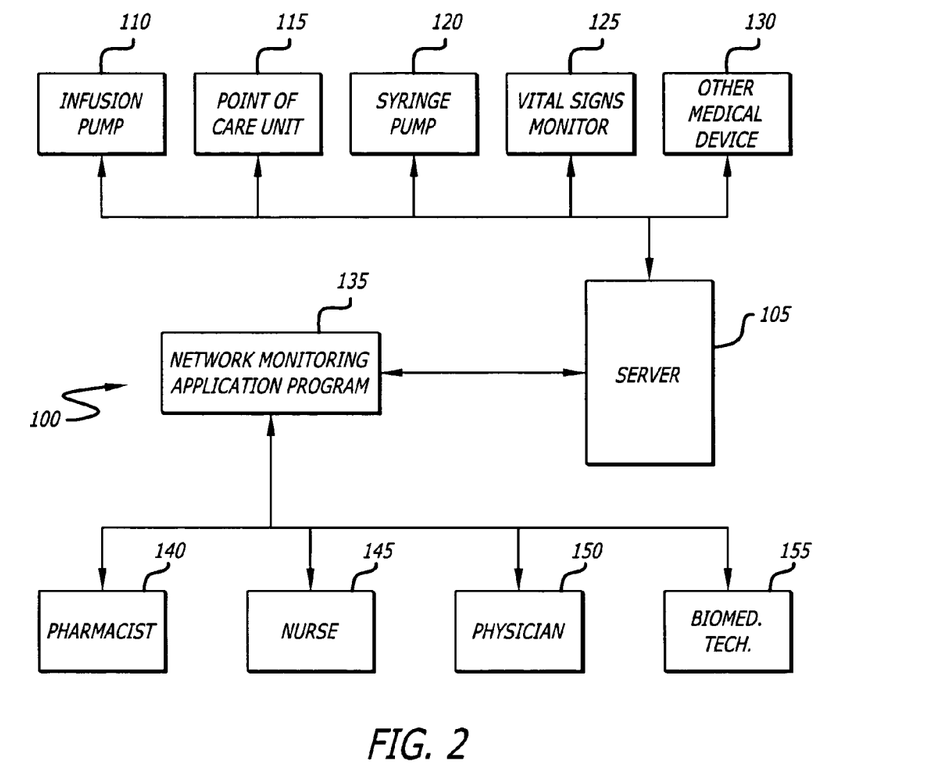
FIG. 2. is a graphical illustration of a network illustrating principles of the present invention.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or alternatively through RS232 links, MIB systems, RF links such as BLUETOOTH (Amtel Corp., San Jose, Calif.), IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. Preferably, the communication means is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within patient care device 12 itself FIG. 2 is a block diagram depicting the information flow between various elements of an institutional patient care system 100 configured in accordance with aspects of the present invention. As shown, server 105 is in communication with various patient related assets, such as an infusion pump 110, a point of care unit 115, a syringe pump 120, a vital signs monitor 125, or other medical device 130. Each of these patient related assets provide therapy to a patient or monitor the patient's vital signs or condition, and provide information about the status of the patient and the patient's therapy to the server. A network monitoring application program 135 provides an interface with the server, and thus all of the assets in communication with the server. Using the network application program 135, users such as a pharmacist 140, nurse 145, physician 150 and biomedical technician 155 may view the information provided to the server 105 by the various patient assets, may adjust the therapy being provided to the patient, or may monitor the operation of the patient assets. Such a system is particularly useful in that it provides a pathway for the software configurations of the patient assets to be altered or updated by a qualified biomedical technician 155. Examples of point of care units and operative modules, vital signs monitors and other clinical devices that may be used with such a system are found in U.S. Pat. No. 5,957,885 to Bollish et al.; US Publication No. U.S. 2003/0106553 A1 to Vanderveen; U.S. Pat. No. 5,681,285 to Ford et al.; and U.S. Pat. No. 5,713,856 to Eggers et al., which are hereby incorporated by reference in their entirety.

A client-server environment incorporating aspects of the present invention typically includes a central server that is accessible by at least one client via a computer network. In more complex systems, the central server may be accessible by at least one local server via a computer network, such as, for example, an Ethernet, wireless network, or the Internet which may in turn be accessed by a client. A variety of computer network transport protocols including, but not limited to TCP/IP, can be utilized for communicating between the central server, any local servers, and client devices configured with a communications capability compatible with the communication protocol used on the network.

The central server generally includes a central database, such as the Microsoft® SQL Server application program, version 6.5 (available from Microsoft, Inc., Redmond, Wash.) or the like, executing thereon. The central server may ensure that the local servers are running the most recent version of a knowledge base, and also may store all patient data and perform various administrative functions including adding and deleting local servers and users to the system. The central server may also provides authorization before a local server or client medical device can be utilized by a user. As stated previously, in typical integrated systems, patient data is preferably stored on the central server, thereby providing a central repository of patient data. However, it is understood that patient data can be stored on a local server or on local storage media, or on another hospital or institutional server or information system, where it may be accessed through the various elements of the system, that is, by local servers or clients, as needed.

Each local server typically serves multiple users in a geographical location. Examples of such a local server include servers located in hospital wards, at nurse stations or at off-site or remote locations operating either as primary or back-up information collection, routing, analysis and/or storage systems. Each local server typically includes a server application, one or more knowledge bases, and a local database. Each local server may also include an inference system capable of interacting with sets of rules or practice criteria for ensuring that proper medical and medication delivery and prescribing practices are followed. Each local server may also perform artificial intelligence processing for carrying out operations of the present invention. When a user logs on to a local server via a client, the user is preferably authenticated via an identification and password, as would be understood by those skilled in the art. Once authenticated, a user is permitted access to the system and certain administrative privileges are assigned to the user. Alternatively, the system may be programmed to operate such that various patient, care-giver and medication identification devices, such as bar coded labels, RF identification tags or devices, or other smart, passive or active identification devices may be used to identify users of the systems and allow access to the system for diagnosing and treating patients.

Each local server may also communicate with the central server to verify that the most up-to-date version of the knowledge base(s) and application(s) are running on the requesting local server. If not, the requesting local server downloads from the central server the latest validated knowledge base(s) and/or application(s) before a user session is established. While in some embodiments of the present invention most of the computationally intensive work, such as data and artificial intelligence processing, is performed on a local server, allowing "thin" clients (that is, computing devices having minimal hardware) and optimizing system speed, the present invention is also intended to include systems where data processing and rules processing is carried out on the clients, freeing the central system, or local server, from such tasks.

Each local client or medical device also includes a client application program that typically consists of a graphical user interface (GUI), although such is not necessary on many medical devices, and a middle layer program that communicates with central or local servers. Program code for the client application program may execute entirely on the local client, or it may execute partly on the local client and partly on the central or local server.

Computer program code for carrying out operations of the present invention is preferably written in an object oriented programming language such as, for example, JAVA®, Smalltalk, or C++. However, the computer program code for carrying out operations of the present invention may also be written in conventional procedural programming languages, such as the "C" programming language, in an interpreted scripting language, such as Perl, or in a functional (or fourth generation) programming language such as Lisp, SML, Forth, or the like. The software may also be written to be compatible with HLA-7 requirements.

Exemplary embodiments of the present invention will now be discussed. Typically, medical devices incorporating aspects of the present invention will be equipped with a Network Interface Module (NIM), allowing the medical device to participate as a node in a network. While for purposes of clarity the present invention will be described as operating in an Ethernet network environment using the Internet Protocol (IP), it will be understood by those skilled in the art that concepts of the present invention are equally applicable in other network environments, and such environments are intended to be within the scope of the present invention.

All direct communications with medical devices operating on a network in accordance with the present invention are performed through a central server, known as the remote data server (RDS). In accordance with aspects of the present invention, network interface modules incorporated into medical devices such as, for example, infusion pumps or vital signs measurement devices, ignore all network traffic that does not originate from an authenticated RDS. The primary responsibilities of the RDS of the present invention are to track the location and status of all networked medical devices that have NIMs, and maintain open communication channels with them.

Figure 3:
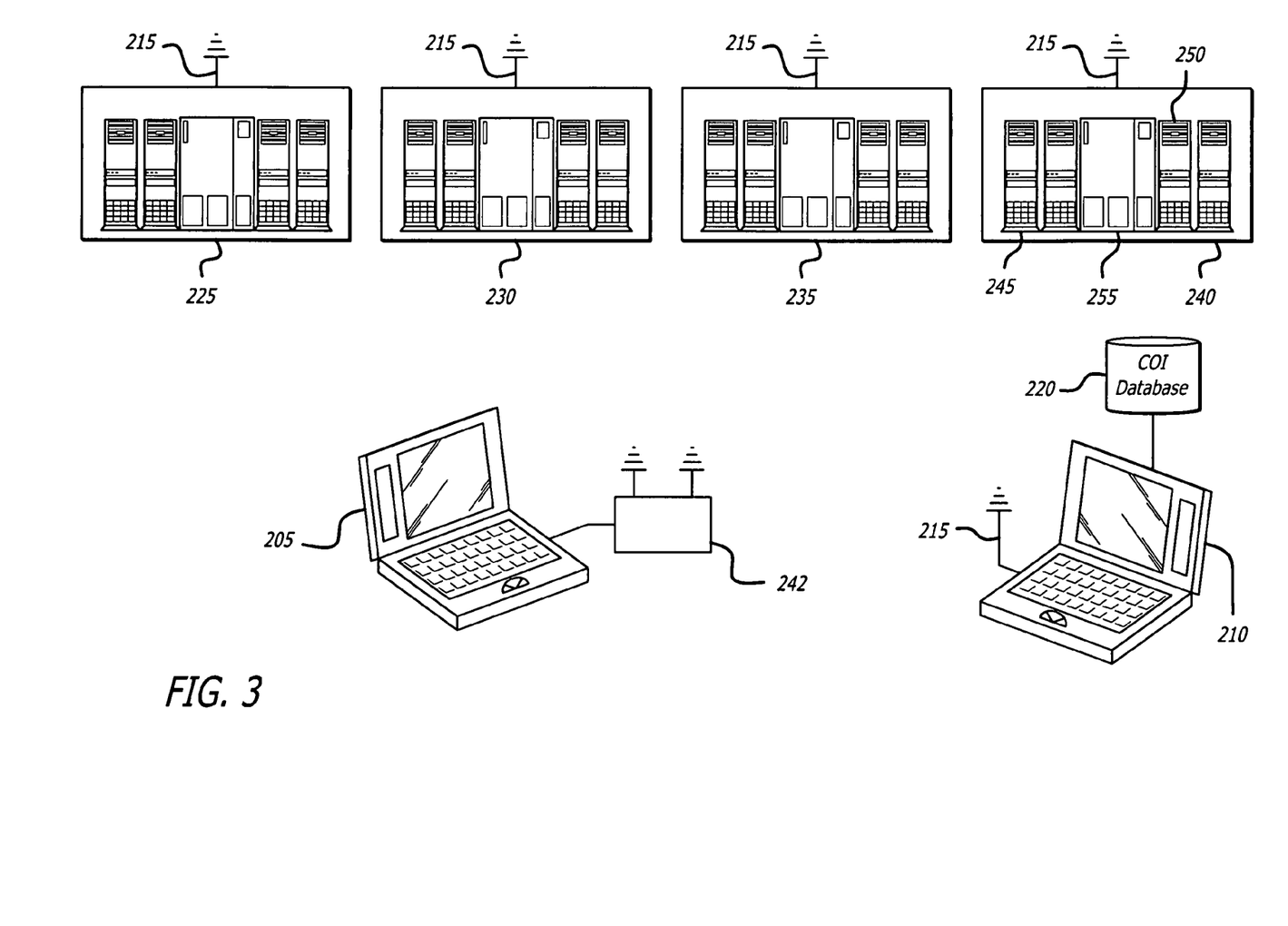
FIG. 3 is a schematic diagram illustrating an embodiment of the present invention incorporating mobile servers communicating with an institution's network through a wireless access point to communicate with medical devices also connected to the network through wireless access points.

In another embodiment, a system in accordance with the present invention consists of mobile servers configured to communicate with mobile devices using wireless access points. As depicted in FIG. 3, the mobile server 205, 210 of this embodiment may be a RDS server, or it may be a server having another function, such as control of a database or other institutional information system. Such a server will typically have the same or equivalent software (kernel) as a fixed server and may be thought of as a mobile systems manager. In one embodiment, the mobile server may exist on a laptop computer, such as shown in FIG. 3 and identified by numerals 205 and 210, a suitably equipped PDA or other mobile computing system.

Communications with the wireless network may be through a wireless access point 215 or module 242, which may be integral with the mobile server and in operable communication with the mobile server, or rover, and using suitable communication hardware, such as an antenna. Utilizing such a wireless communication network, the mobile server 205, 210 may access a CQI database 220, a rule database (not shown), or other database (See FIG. 1) having general or patient specific information incorporated therein. Alternatively, the mobile server 205, 210 may be connected to a separate wireless access module 242. Such a connection may be through a port on the server, such as a USB or other suitable connection.

Using wireless access points 215, 242 operating at, for example 2.2 GHz, or other suitable frequency, and suitable interface equipment, the mobile server 205, 210 is thus capable of communicating in two directions with and, if desired, controlling mobile clients 225, 230, 235 and 240 such as appropriately equipped and programmed infusion pumps 245 or other medical devices, such as vital signs monitoring or laboratory equipment 250. Thus, the mobile server 205, 210 of the present invention eliminates the need for having a dedicated room or server that is stationary and incapable of being easily moved to a different location.

Figure 4:
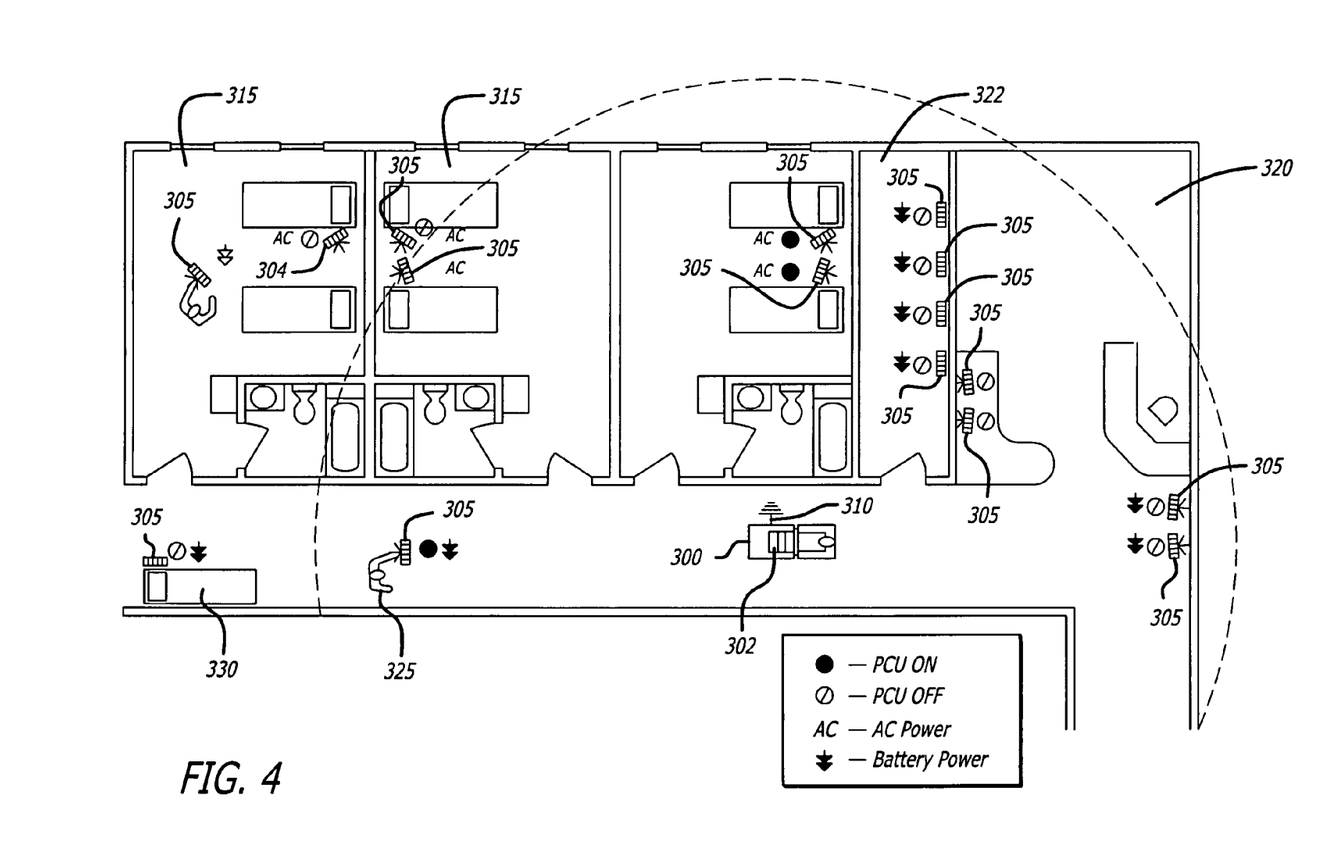
FIG. 4 is an example of the application of a mobile server in a clinical setting showing a mobile remote server on a push cart.

An example of the application of such a mobile server is shown in FIG. 4 where such a system is placed on a push cart. In this example, various medical devices 305 capable of communicating with a mobile server 302 in accordance with the principles of the present invention are located throughout a typical clinical facility. As shown, some of these units may be located at a patient's bedside 315, at a nurse's station 320, in a storage area 322, or may be configured as ambulatory devices that can accompany a patient 325 as the patient moves about the facility or may accompany a patient 330 as the patient is wheeled throughout the facility on a gurney. As the mobile server 302 mounted on a cart 300 is pushed through the facility, it broadcasts message beacons to all clinical devices, be they infusion pumps, device controllers controlling multiple devices, or vital signs monitoring devices that are equipped with appropriate wireless access equipment and network interface modules (NIMs). As depicted, the mobile server 302 may be equipped with more than one kind of wireless communication means 310. For example, the mobile server may communicate using an 802.11 WIFI protocol or may use an RF or IR transmitter or receiver. Those skilled in the art will understand that any wireless means may be used, as described in more detail above.

FIG. 4 shows a layout view of one type of hospital ward showing patient rooms, nurse station, storage facility, hallways, medical devices at patients' bedsides including infusion pumps and vital signs monitors, and a mobile server (mobile systems manager) 302. The clinical setting where such a system may be employed may consist of various types of patient wards, such as an ICU (intensive care unit), labor and delivery, and medical/surgical unit. In the case of FIG. 4, the medical instruments are configured according to the specific clinical setting, that is, the medical instruments are configured as appropriate for a specific ward or unit type, and are programmed with specific ward-related operating parameters such as alarm levels, maximum rates, dose limits and the like. These ward-related operating parameters are referred to herein as "profiles." The profiles may be given names similar or identical to the relevant patient ward names such as ICU, labor and delivery, and so forth. The term "PCU" is meant to indicate "patient care unit" and may comprise various medical devices such as an infusion pump, a vital signs monitor, or other devices.

As the cart and mobile server 302 travels through the facility, the mobile server transmits a beacon signal that may be received and responded to by any device equipped with a suitable NIMs that is within range of the mobile server wireless transmitter/receiver. In one embodiment where a WIFI protocol is used, the range will be approximately thirty feet, that is, all devices within a radius of thirty feet of the mobile server 302 may receive the beacon signal and reply accordingly to set up a secure communication session with the mobile server. As those familiar with such technology understand, the range depends on the protocol, as well as the particular hardware used, and may be greater or lesser than thirty feet, as desired.

As described above, devices in range of the mobile server that are currently "awake" and operating may respond to the beacon signal. Alternatively, as described above, the NIMs of various devices may be programmed to listen for a beacon signal, and then awaken the device so that data may be exchanged between the device and the mobile server. In yet another embodiment, the NIM may be programmed to communicate with the mobile server and exchange information with the server without awakening the clinical device to improve battery live of the device.

One embodiment of the present invention includes a network monitoring application program comprising suitable software programming that runs on a server (FIG. 1) or other computer accessible through the network. The network monitoring application program includes modules that monitor the status of medical and clinical devices and gathers information for analysis and report generation from those devices. The network monitoring application program also contains interface modules that allow a user to interface with the system to view data, change operating parameters of medical and clinical devices in communication with the network, and to display medical and clinical device information to the user using a variety of graphical displays.

Figure 5:
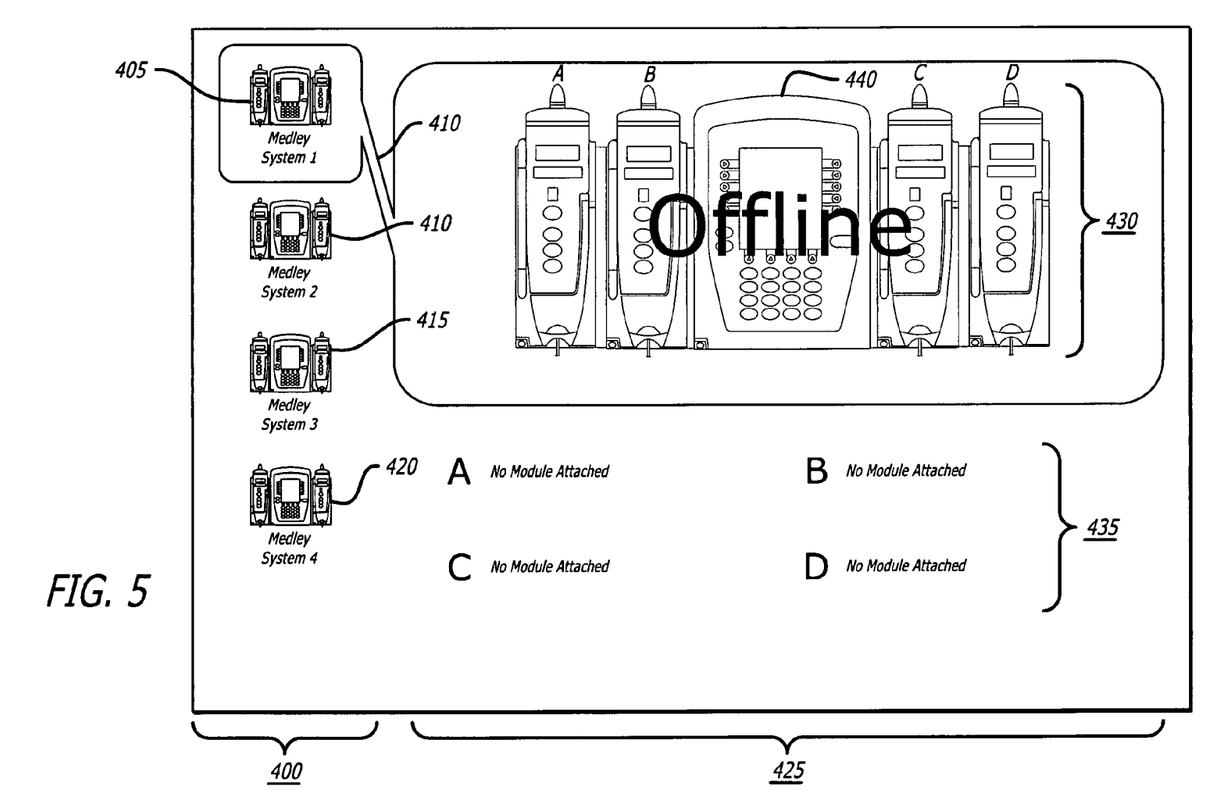
FIGS. 5-9 are graphical displays illustrating various information displayed by the monitoring system of an embodiment of the present invention.

FIG. 5 depicts one of the numerous screen displays generated by the network monitoring application program for users' viewing and interaction. The display consists of two portions, the first portion being a left-hand screen portion 400 containing standard icons 405, 410, 415 and 420 representing medical and clinical devices that have been registered with the server, along with text information that provides an identification of the medical and clinical device. The identifying information may include, for example, location of the device, patient name, pump name, a warning or other information.

The second portion of the display is a right-hand screen portion 425. Portion 425 includes a portion 430 that displays an enlarged graphic depicting the actual physical medical instrument selected for display. A textual display portion 435 is located below portion 430 and includes text information related to the status and profile of the medical instrument and relevant programming parameters. For example, device 405 has been selected using an appropriate selection means, such as a touch screen, mouse or other selection device. Portion 430 displays an enlarged graphic of the selected device, in this example, a patient care unit 440 that includes clinical device modules "A", "B", "C" and "D". Clinical device modules "A", "B", "C" and "D" may be, for example, infusion pumps, vital signs monitors, a bar code reader or other device. In the example displayed, however, no modules are attached to patient care unit 440. In such a case, the graphical display of modules "A", "B", "C" and "D" may be grayed out to indicate they are not attached. By "not attached", it is meant that either the devices are not physically attached to patient care unit 440, or the entire device is powered down and offline, or one or more individual modules are powered down, and thus are not considered to be "attached" to the network. The status of modules "A", "B", "C" and "D" are also shown in portion 435.

Also shown is the selection indicator used by the network application program which in this case surrounds the standard icon at the left of the screen with a square having rounded corners. Once the user selects one of the standard medical device icons in the left-hand portion 400 of the screen, the selection indicator appears around that selected icon. As a result of the selection, a larger selection indicator box appears to the right with status of the selected medical device. The two boxes are interconnected with a lead line 445 comprising two parallel straight lines extending approximately between the centers of the adjacent sides of the boxes.

Figure 6:
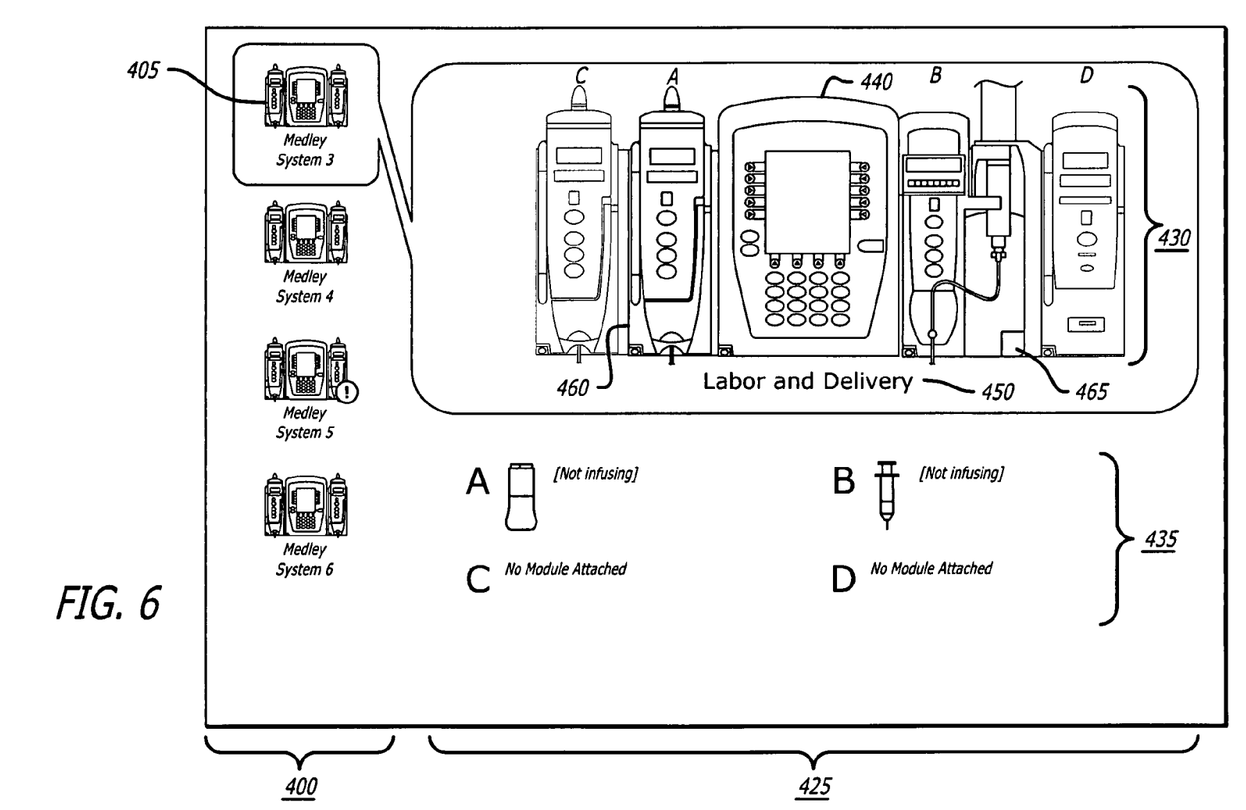

FIG. 6 depicts another screen display generated by the network monitoring application program. This display indicates that the user has selected standard medical device icon 405 located at the left portion 400 of the screen of a medical device, here indicated as "Medley System 3."

The larger selection indicator box shows a more detailed depiction in screen portion 430 of the actual medical device selected using icon 405. In this example, the instrument shown is a Medley Point of Care Unit having two modules attached, one being a syringe pump, module A and a large volume pump ("LVP"), module "B." It should be noted that the ordering of the modules, that is, the location of modules "A", "B", "C" and "D" relative to unit 440 is not fixed. In other words, the modules may be located and labeled as desired by the user of the equipment, and registered appropriately with unit 440 by making suitable inputs to unit 440.

A text box 450 indicates the profile, or configuration, of Medley System 3 (unit 440). In this example, the unit 440 is configured for use in the Labor and Delivery unit of the institution. This means that various operating parameters, which may also include drug libraries or libraries of specific guidelines for providing appropriate patient care, such as dosage limits and the like, appropriate for use in the a Labor and Delivery unit have been loaded into the medical device.

Immediately beneath portion 430 containing the graphic depiction of the selected device is portion 435 containing text indicating the profile of the device shown within the selection indicator box. Outside the selection indicator box is further specific text information about the status of the instrument and/or modules. In this case there are two modules, "A" and "B", and specific information about each module is given. In this case, both modules are indicated to be "Not Infusing." Similarly, modules "C" and "D" are indicated as "No Module Attached."

Figure 7:
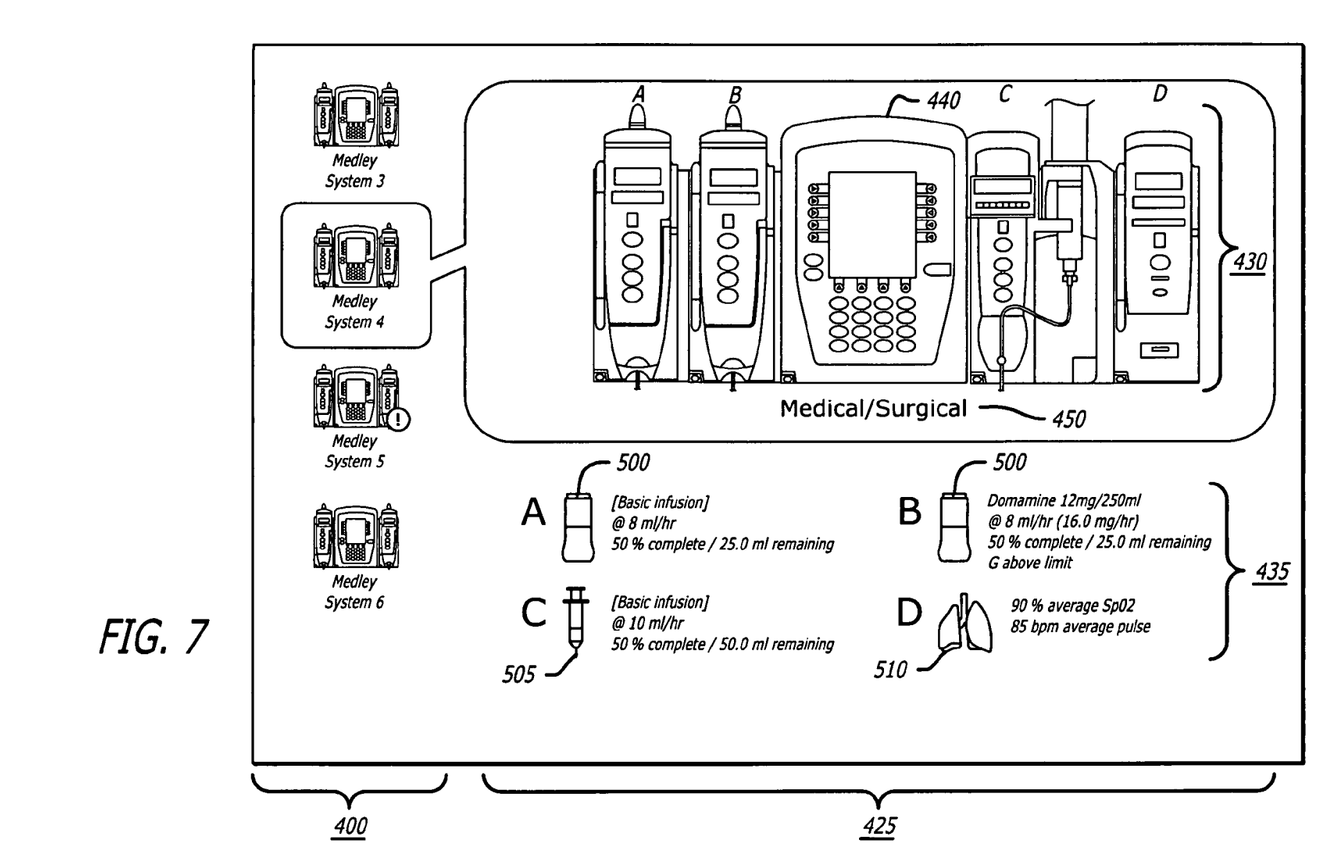

FIG. 7 is a graphic depiction of a display screen showing the selection of "Medley System 4" from the standard icons at the left-hand side portion 400 of the screen. As shown by the graphical display in portion 430 of the screen, this instrument has four modules, modules "A" and "B", which are LVP's, located to the left of the Medley Point of Care unit 440, module "C", a syringe pump, located immediately to the right of unit 440, and module "D", a pulse oximetry module, located at the far right of unit 440. The text in box 450 indicates that "Medley System 4" is configured for use in a "Medical/Surgical" unit of the institution.

Portion 435 of the display contains further information concerning each module or "channel." As will be readily understood by those skilled in the art, the terms "module" and "channel" may be interchanged without changing their meaning or function, as those terms are used herein. As shown in portion 435 of the screen, the information displayed for channel (module) "A" includes an icon 500, which represents a medication container or bag of solution to be infused by the LVP of channel "A". The software of the monitoring program may also include programming that displays the icon 500 in such a way that the level of fluid shown in the icon represents the level of medication remaining in the container. To the right of icon 500 is text indicating the type of drug being infused, in this case, a basic infusion, and dosing parameters, "8 ml/hr."

The text further clarifies the percentage of the drug delivered ("50% complete") and the quantity remaining ("25.0 ml remaining"). Other information may be displayed as appropriate.

Moving now to module "B", the same type of information is presented. In this channel, the drug Dopamine is indicated by the displayed text as being infused. However, in this channel, an icon of the letter "G", designed to draw attention to the icon accompanying the text "above limit" is displayed. This "G" icon indicates the unit has been configured with a program monitoring the values of pumping parameters programmed into the pump, and which provides a warning, which may be either visual, audio or both, that one or more parameters entered into the device to program the operation of the device is outside of a predetermined range established by the institution. The "G" icon may also be enhanced using various attributes, such as bold, flashing, or color, to increase its ability to draw the attention of a care giver to the icon.

One such program having this capability is known as the GUARDRAILS® program made available by ALARIS Medical Systems, Inc. in San Diego, Calif. In particular, the GUARDRAILS program references a drug library located in the pump, point of care unit, server, or elsewhere, that has a data set(s) relevant to a particular drug or treatment, in this case, Dopamine. In this example depicted in FIG. 7, the "G" icon followed by the text "above limit" warns that the GUARDRAILS program has detected a pumping parameter that is outside an acceptable range for Dopamine, that is, "above limit."

Also shown in FIG. 7 is a syringe icon 505 representing the medical fluid container loaded into the syringe pump of module "C." Similarly, a lung icon 510 is displayed indicating that the device of channel "D" is a pulse oximetry module. Other icons or methods or identification may be used. The figures herein provide only examples.

Figure 8:
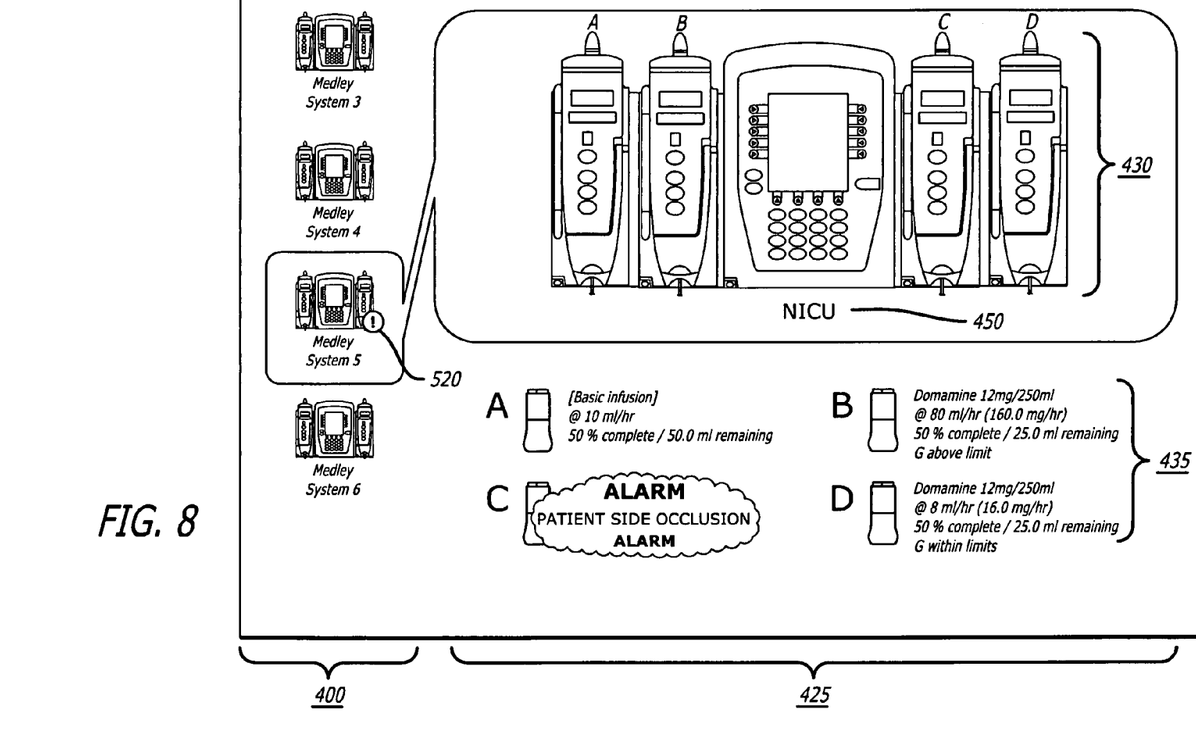

Referring now to FIG. 8, the box surrounding the icon labeled "Medley System 5" indicates that that system has been selected. The contents of box 450 indicates that the profile for this system is configured for use as "NICU", that is, neo-natal intensive care unit. The selected icon in portion 400 of the screen includes a warning indicator in the form of a circle with an exclamation mark, indicating that a condition associated with the selected system exists that may require attention by a care giver. Although a circle with an exclamation mark is used in this example, other warning indicators may be used. Moreover, different warning indicators may be used to indicate different types of conditions associated with the selected system. This warning indicator is advantageous in that it allows a care giver or other user of the system to see at a glance which systems in communication with the network administration program require attention.

The information presented in portions 430 and 435 of the display are similar to the information presented in other figures. However, the reason for the warning indicator associated with the icon in portion 400 of the display can now be seen. In this example, channel "C" is alarming due to a detected "alarm, patient side occlusion detected alarm." This is shown by a rectangle superimposed over the text in portion 435 of the display. This rectangle may include other attributes designed to attract attention to the alarm. For example, the superimposed rectangle may be flashing, or it may be shaded or colored with a color such as red to increase its ability to draw the attention of a care giver to the warning. The edges of the rectangle may also fade so that more of the underlying text concerning the status and pumping parameters of the channel can be read. Of course, other shapes besides a rectangle may be used to indicate a warning, or specific shapes or colors or other attributes may be used to indicate specific warning types or the severity of a warning without departing from the scope of the invention.

Referring again to portion 435 of FIG. 8, the text associated with channel "D" also has a "G" icon indicating that the GUARDRAILS program is monitoring the parameters associated with the drug Dopamine. In this case however, the text following the "G" icon indicates that the pumping parameters are "within limits." It should be noted that in FIG. 7, the same drug was being infused with the same pumping parameters but the GUARDRAILS program indicated that at least one of the infusion parameters was "out of limits." While a comparison of the channels in FIGS. 7 and 8 indicate that the dosing parameters associated with the delivery of Dopamine are the same, the reason that the "G" indicates the delivery is within limits in FIG. 8 is due to the configuration of the system for use in the NICU, as opposed to the profile for the system of FIG. 7, which is configured for use in a "medical/surgical" unit. Thus, it will be apparent that different limits for a given drug may be applied by the GUARDRAILS program depending on the configuration of the system.

Figure 9:
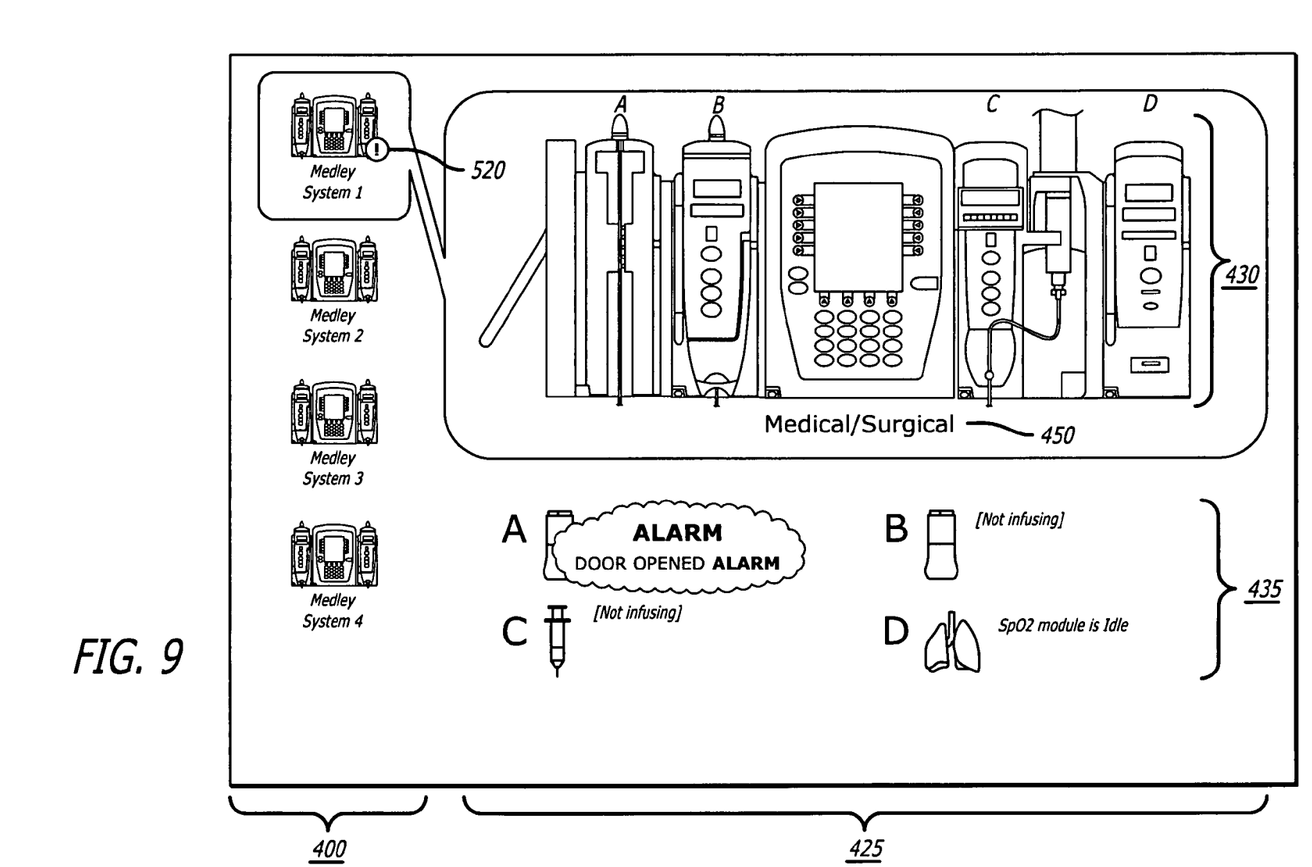

Turning now to FIG. 9, a different alarm is shown. In this case, a "door open alarm" is being indicated for the pump associated with channel "A." The large graphic of the pump associated with channel "A" shown in portion 430 of the screen also shows that the door of the pump associated with channel "A" is open. Other graphical devices can be used on the display to provide a visual display of the status of various elements of the system, thus assisting care givers in ensuring that the system is operating correctly.

While several forms of the invention have been illustrated and described, it will also be apparent that various modifications can be made without departing from the spirit and scope of the invention. Accordingly, it is not intended that the invention be limited except by the appended claims.

We claim:

1. A medical monitoring system, comprising:
at least one infusion pump comprising at least one removable treatment module capable of delivering a medication to a patient;
a server in communication with the at least one infusion pump;
a display screen; and
a processor in communication with the server and the display, the processor configured to monitor information communicated by the at least one infusion pump representative of a status of the at least one infusion pump, the processor further configured to generate a graphical display for communicating the information to a user, the graphical display including a plurality of portions comprising:
a first portion including at least one icon readily understood by the user to represent the at least one infusion pump,
a second portion not overlapping with the first portion, the second portion including a graphic for a selected icon, the graphic being larger than the icon, depicting the actual physical appearance of the current configuration of at least one infusion pump associated with the selected icon including the specific at least one treatment module included in the at least one infusion pump.

2. The system of claim 1, wherein the at least one treatment module is one of the set of an infusion pump, a syringe pump, a patient-controlled anesthesia (PCA) pump, an epidural pump, and an enteral pump.

3. The system of claim 2, wherein the graphical display further includes information on the operating settings of the at least one treatment module.

4. The system of claim 3, wherein the processor is further configured to compare a value of a parameter associated with the status of the at least one infusion pump with a database of rules to determine if the value of the parameter is within a range of values defined by a rule in the database of rules, and if the value of the parameter is not within the range of values, generate a warning symbol in proximity to the icon representing the at least one infusion pump.

5. The system of claim 1, wherein the infusion pump further comprises at least one monitor module capable of monitoring a condition of the patient.

6. The system of claim 5 wherein the monitor module is a pulse oximeter.

7. The system of claim 5 wherein the monitor module is one of the set of a blood pressure monitor, an electrocardiogram (EKG) monitor, an electroencephalogram (EEG) monitor, a heart rate monitor, and an intracranial pressure monitor.

8. A medical device monitoring system, comprising:
an infusion pump comprising:
a central processing unit (CPU);
at least one removable module coupled to the CPU, each module being capable of delivering a medication or sensing a patient condition; and
a computer in communication with the infusion pump, the computer configured to receive information from the infusion pump representative of the status of the at least one coupled module, and generate a visual display of the received information, the visual display having a first portion comprising an icon readily understood by a user to be representative of the infusion pump and a second portion comprising a depiction of the actual physical appearance of the CPU and the at least one coupled module;
wherein the computer further includes means for accessing rules stored in a database of rules, the rules including ranges of values for operating parameters of the infusion pump, and wherein the computer is further configured to compare values of the information received from the infusion pump to the rules stored in the database of rules and generate a warning graphic proximate to the icon representative of the infusion pump if a value of a selected operating parameter of the received information is not within the range of values contained in a selected rule.

9. The system of claim 8, wherein the computer is a mobile server capable of moving about a facility wherein the infusion pump is located.

10. The system of claim 8, wherein at least one portion of the display provides a textual description of the status of the infusion pump.

11. The system of claim 8, wherein the first portion of the display includes a textual description of the status of the infusion pump.

* * * * *